(12) United States Patent
Gruskin

(10) Patent No.: US 6,387,363 B1
(45) Date of Patent: May 14, 2002

(54) BIOCOMPATIBLE MEDICAL DEVICES

(75) Inventor: Elliott A. Gruskin, Killingworth, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 07/999,517

(22) Filed: Dec. 31, 1992

(51) Int. Cl.[7] .................. A61K 31/715; A61K 9/14; A61K 47/32; A61F 2/00
(52) U.S. Cl. ............... 424/78.37; 424/426; 424/422; 424/486; 424/423; 514/772.4
(58) Field of Search .................. 424/426, 428, 424/422, 423, 486, 78.31, 78.37; 514/772.4

(56) References Cited

U.S. PATENT DOCUMENTS

| | | |
|---|---|---|
| 2,668,162 A | 2/1954 | Lowe |
| 2,683,136 A | 7/1954 | Higgins |
| 3,268,486 A | 8/1966 | Klootwijk |
| 3,268,487 A | 8/1966 | Klootwijk |
| 3,630,205 A | 12/1971 | Listner |
| 3,736,646 A | 6/1973 | Schmitt et al. |
| 3,773,919 A | 11/1973 | Boswell et al. |
| 3,781,349 A | 12/1973 | Ramsey et al. |
| 3,784,585 A | 1/1974 | Schmitt et al. |
| 3,846,382 A | 11/1974 | Ramsey et al. |
| 3,867,190 A | 2/1975 | Schmitt et al. |
| 3,875,937 A | 4/1975 | Schmitt et al. |
| 4,045,418 A | 8/1977 | Sinclair |
| 4,052,988 A | 10/1977 | Doddi et al. |

(List continued on next page.)

FOREIGN PATENT DOCUMENTS

| | | |
|---|---|---|
| DE | 2062604 | 12/1970 |
| GB | 1332505 | 10/1973 |

OTHER PUBLICATIONS

Chem. Ab. 111:174683a Ibay et al.*
Anthony–Cahill, et al., Site–Specific Mutagenesis With Unnatural Amino Acids, Elsevier Science Publishers, Ltd. (UK) (1989).
Ellman, et al., Site–Specific Incorporation of Novel Backbone Structures into Proteins, Science (Jan. 1992).
Fournier, et al., Genetic Synthesis of Periodic Protein Materials, Journal of Bioactive and Compatible Polymers, vol. 6 (Oct. 1991).
Heckler, et al., T4 RNA Ligase Mediated Preparation of Novel "Chemically Misacylated" tRNA, American Chemical Society (1984).
Heckler, et al., Preparation of 2'(3')–0–Acyl–pCpA Derivatives As Substrates For T4 RNA Ligase–Mediated "Chemical Aminoacylation", Tetrahedron, vol. 40, No. 1, pp. 87 to 94 (1984).
Fahnestock, et al., Ribosome–Catalyzed Polyester Formation, Science (Jul. 23, 1971).
Fahnestock, et al., Formation of a Ternary Complex of Phenyllactyl–tRNA with Transfer Factor Tu and GTP, Biochim. Biophys. Acta, 269 (1972) 62–66.
Gilding, et al., Biodegradable Polymers for Use in Surgery—Polyglycolic/Poly (Actic Acid) Homo– and Copolymers:1, Polymer, 1979, vol. 20, Dec.
Mendel, et al., Construction of a Ligase Activated Protein by Unnatural Amino Acid Mutagenesis, 1991, American Chemical Society.

(List continued on next page.)

Primary Examiner—Thurman K. Page
Assistant Examiner—Blessing Fubara

(57) ABSTRACT

Biocompatible medical devices, including sutures, are disclosed which are produced from polyesters formed from lactide and glycolide copolymers. In a preferred mode of the invention, the biocompatible medical devices are absorbable.

12 Claims, 5 Drawing Sheets

U.S. PATENT DOCUMENTS

| | | |
|---|---|---|
| 4,057,537 A | 11/1977 | Sinclair |
| 4,137,921 A | 2/1979 | Okuzumi et al. |
| 4,157,437 A | 6/1979 | Okuzumi et al. |
| 4,243,775 A | 1/1981 | Rosensaft et al. |
| 4,279,249 A | 7/1981 | Vert et al. |
| 4,300,565 A | 11/1981 | Rosensaft et al. |
| 4,523,591 A | 6/1985 | Kaplan et al. |
| 4,744,365 A | 5/1988 | Kaplan et al. |
| 4,839,130 A | 6/1989 | Kaplan et al. |
| 4,844,854 A | 7/1989 | Kaplan et al. |
| 4,911,165 A | 3/1990 | Lennard et al. |
| 5,019,093 A | 5/1991 | Kaplan et al. |
| 5,037,429 A | 8/1991 | Hermes et al. |
| 5,066,772 A | 11/1991 | Tang et al. |
| 5,124,103 A | 6/1992 | Kaplan et al. |
| 5,145,945 A * | 9/1992 | Tang et al. ............... 528/354 |
| 5,248,761 A | 9/1993 | Hermes |
| 5,256,762 A * | 10/1993 | Hermes et al. ............. 528/361 |

OTHER PUBLICATIONS

Noren, et al., A General Method for Site–Specific Incorporation of Unnatural Amino Acids into Proteins, Science, vol. 244, (Apr. 14, 1989).

Robertson, et al., A General and Efficient Route for Chemical Aminoacylation of Transfer RNAs, 1991 Chemical Society.

Tirrell, et al., Genetic Engineering of Polymeric Materials, MRS Bulletin (Jul. 1991).

Ibay, A. C., Chemical Abstracts, vol. 111, No. 20, p. 1, Ref No. 174683a, Nov. 13, 1989.

* cited by examiner

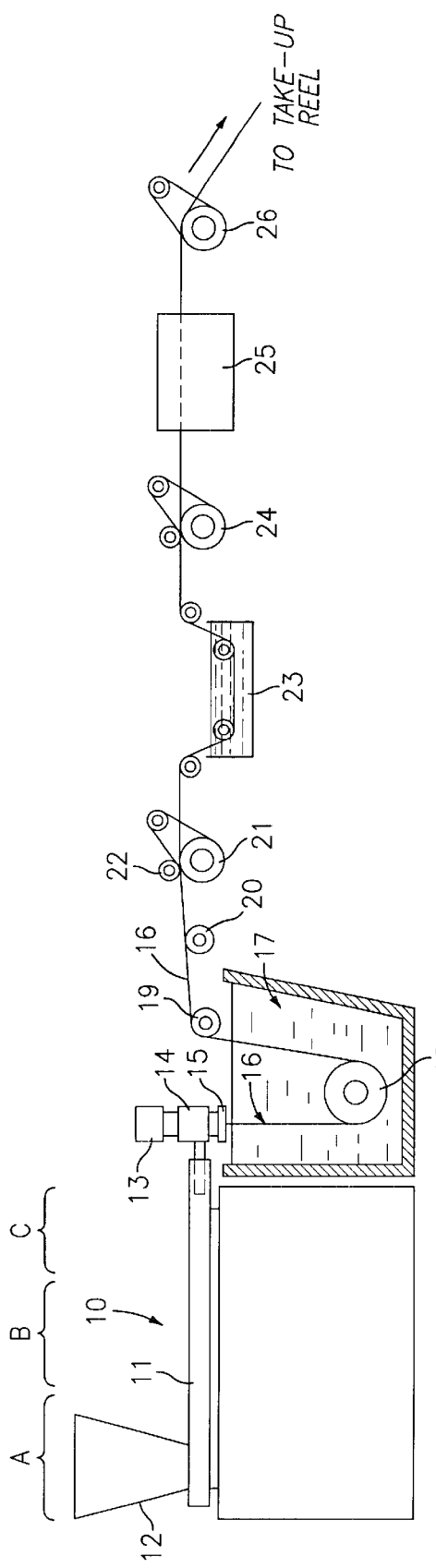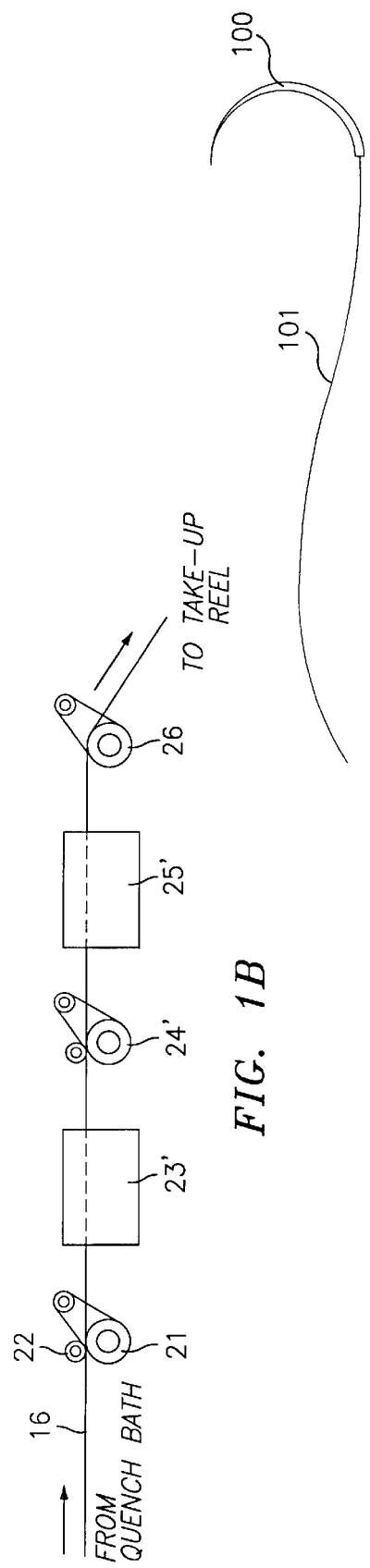

tRNA–ALANINE            tRNA–GLYCINE
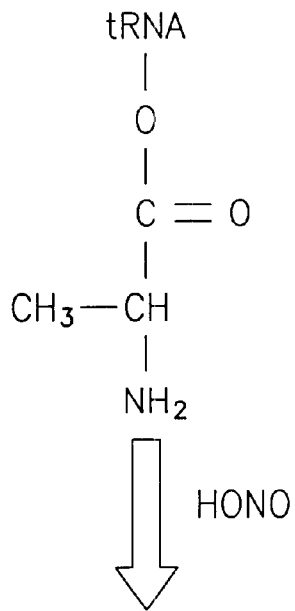 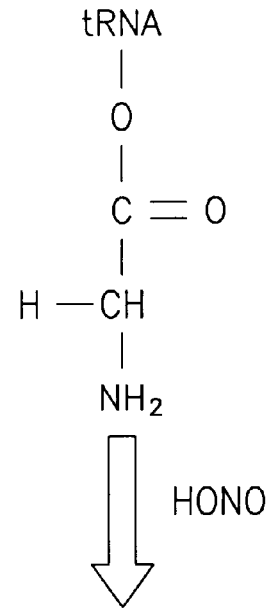
tRNA–LACTATE            tRNA–GLYCOLATE
*FIG. 6*

BIOCOMPATIBLE MEDICAL DEVICES

BACKGROUND OF THE INVENTION

1. Field of the Invention

The present invention relates to biocompatible medical devices such as sutures and the like which also may be absorbable and to methods of making them.

2. Description of the Background Art

The advantages of absorbable materials in surgical applications are universally appreciated. The traditional naturally derived suture, known as "catgut," is formed from collagenous material obtained from sheep or beef intestine. More recently, synthetic absorbable sutures of varying chemical composition have been developed.

A number of synthetic polymers have been described for use in making sutures and other bioresorbable medical devices. Effective synthetic absorbable sutures, as well as other medical devices such as haemostatic aids, intraosseous implants, slow-release drug delivery systems, and tissue regeneration devices including nerve channels, sperm ducts, vascular graphs, Fallopian tube ducts and the like, must satisfy a number of biological, physical and chemical requirements. Among these requirements are that the material be bioresorbable, non-carcinogenic, non-antigenic, and non-toxic.

Further, satisfactory bioresorbable polymers for medical applications need to have appropriate mechanical properties including flexibility, tensile strength, dimensional stability, should be sterilizable and absorbable by living tissue at a uniform rate. With respect to sutures, flexibility, adequate straight tensile and knot strength and the capability of being properly and easily tied in surgical knots are particularly desirable characteristics.

Various synthetic polymers have been proposed for use in the fabrication of sutures and other medical devices. Of particular interest are homopolymers and especially copolymers of lactic acid and glycolic acid. Such copolymers have been developed in an attempt to combine the characteristics of both compounds and extend the range of polymer properties and rates of hydrolysis. For example, poly-L-lactic acid is hydrolyzed more slowly than polyglycolic acid and copolymers of the two acids can be made to hydrolyze at intermediate rates. Polymers of this type, and their use in the preparation of synthetic absorbable sutures, are disclosed, for example, in U.S. Pat. Nos. 2,703,316, 3,468,853, 3,565,869, 3,636,956, 4,137,921, 4,744,365, 4,839,130 and 5,124,103. Improved braided sutures, which may be composed of lactic acid and glycolic acid copolymers, are described in U.S. Pat. Nos. 5,019,093 and 5,037,429.

The use of lactic acid and glycolic acid copolymers in the manufacture of molded medical devices such as, for example, staples or clips is described in U.S. Pat. No. 4,523,591, which describes important and desirable properties for such molded articles. That patent also discloses procedures for injection molding, and other suitable molding techniques are known and employed in the art.

U.S. Pat. No. 3,736,646 discloses sterile synthetic copolymers containing lactic acid and glycolic acid having enhanced tissue absorption and solubility in organic solvents. That patent also contains reference to a number of other U.S. patents and publications which describe various approaches to the manufacture and use of synthetic polymeric sutures formed from lactic acid and glycolic acid.

Methods of preparing polymers of lactic acid and glycolic acid are described in the patents referred to above. These traditional chemical synthetic methods typically involve the use of a polymerization catalyst which, when combined with appropriately prepared monomer under specified atmospheric and temperature conditions, catalyses the formation of the polymer.

Of course, the way in which a polymer, and especially a copolymer, is made will affect the working characteristics of the resulting suture or other medical device. For example, U.S. Pat. No. 5,066,772, which discloses copolymers of recurring units derived from carbonates, lactides and glycolides, discloses copolymers which can be random copolymers or block copolymers, depending upon the properties desired. Random copolymers are disclosed as preferred where soft, pliable and relatively fast bioresorbable materials are required. Block copolymers are disclosed as preferred where hard, crystalline and relative slow bioresorbing materials are required. The patent contains an extensive description of block copolymers and the manner in which the selection of repeating block units may affect properties of the copolymer such as elasticity, modulus, pliability, hardness, softness, crystallinity and bioresorption rate.

U.S. Pat. No. 4,137,921 discloses a two-stage polymerization process for the preparation of lactic acid and glycolic acid copolymers. The first stage involves a random copolymerization of optically active lactic acid and glycolic acid monomer by conventional means. A second stage consists of further polymerization of the first stage polymer with additional lactic acid and glycolic acid monomer.

One drawback of traditional synthetic methods of producing polymers, such as those set forth in the U.S. patents referred to above, is that they often involve extreme reaction conditions. These include temperatures as high as 180° C. for extended periods of time, use of highly volatile organic solvents such as chloroform and toluene, dry nitrogen reaction atmospheres and high vacuum. Further, these methods require the use of catalysts, some of which may be scarce commodities.

Perhaps the most important disadvantage of prior methods for making synthetic polymers is that they do not allow a high degree of control over the ultimate makeup of the polymer. Traditional chemical synthetic methods of making random copolymers, for example, rely upon crude adjustment of starting material ratios that can, at best, produce a polymer falling somewhere within a broad range of desired characteristics. Similarly, known methods of producing block copolymers are relatively crude, and have the additional disadvantage of requiring tedious and expensive chemical reaction steps.

Copolymer formation also is complicated by the fact that the relative rates of reactivity of glycolide and lactide are different. For example, when equimolar amounts of glycolide and lactide are reacted, glycolide is initially more likely to combine with growing chains than is lactide. Consequently, the initial composition of the growing chain contains a predominance of glycolic acid units occasionally and randomly interspersed with short sequences of lactic acid units. As the reaction proceeds, the concentration of lactide contained in the mixture increases relative to glycolide, and the ratio of glycolic acid units to lactic acid units forming the chain becomes more equal. As the reaction nears completion, most available glycolide has polymerized and the relative amount of lactide is high. Consequently, a larger number of lactic acid units are likely to come together and polymerize.

One consequence of this stoichiometric effect is that the first portion of the copolymer chain is likely to contain a predominance of glycolic acid units, and the end portion of the chain is likely to contain a predominance of lactic acid units. Random sequences generated by the synthesis of poly(lactide-co-glycolide) result in the formation of heterogeneous polymers, i.e., no two polymeric chains are likely to be identically duplicated. Consequently, the physical and chemical properties of such copolymers have been difficult to predict or control with a high degree of precision.

Obviously, optimal control of the properties of a synthetic copolymer material would be attained where the identity of each successive co-monomeric unit was individually and specifically determined from the very outset of the process. It can readily be seen that this would allow an exquisite degree of control, leading to singularly improved biocompatible and absorbable sutures and other medical devices. However, no such method has been described.

Accordingly, it is an object of the present invention to provide improved methods of making lactic acid and glycolic acid copolymers which allow each successive lactic acid or glycolic member of a polymeric chain to be individually and specifically specified. It is another object of the present invention to provide biocompatible and absorbable sutures and other medical devices comprised of lactic acid and glycolic acid copolymers made according to the methods of the invention.

It is a further object of the present invention to allow for the incorporation of individual or multiple amino acids into the polymers made according to the methods of the invention. These can include short or long lengths of amino acids which may have desirable bioactive characteristics. Short or long amino acid sections incorporated into the polymers of the invention may, for example, allow cell attachment, act as growth factors, or prevent thrombosis. Thus, another object of the invention is to provide synthetic copolymer compositions having incorporated therein one or more bioactive elements.

These and other objects of the present invention will be apparent to those of skill who appreciate and understand the teachings of the present specification, set forth in the following description.

SUMMARY OF THE INVENTION

The present invention is directed to biocompatible medical devices, including sutures, produced from polyesters formed by novel synthetic methods for the template driven synthesis of lactic acid and glycolic acid copolymers of defined sequence. The biocompatible medical devices of the invention also may be absorbable. The novel synthetic methods of the invention allow each successive lactic acid or glycolic acid member of the copolymer to be individually specified. This capability provides an unprecedented degree of control over the design and properties of the copolymer product. As a result of the present invention, greatly improved sutures and other medical devices can now be developed and produced.

BRIEF DESCRIPTION OF THE DRAWINGS

FIG. 1A schematically illustrates a monofilament suture manufacturing operation which is especially suitable for producing larger size sutures employing the polymers of the invention.

FIG. 1B schematically illustrates a monofilament suture manufacturing operation which is especially suitable for producing smaller size sutures employing the polymers of the invention.

FIG. 2 illustrates a suture employing the polymers of the invention.

FIG. 6 shows the chemical structure of a polyester of defined sequence I according to the present invention.

DESCRIPTION OF THE PREFERRED EMBODIMENTS

Figure 3:
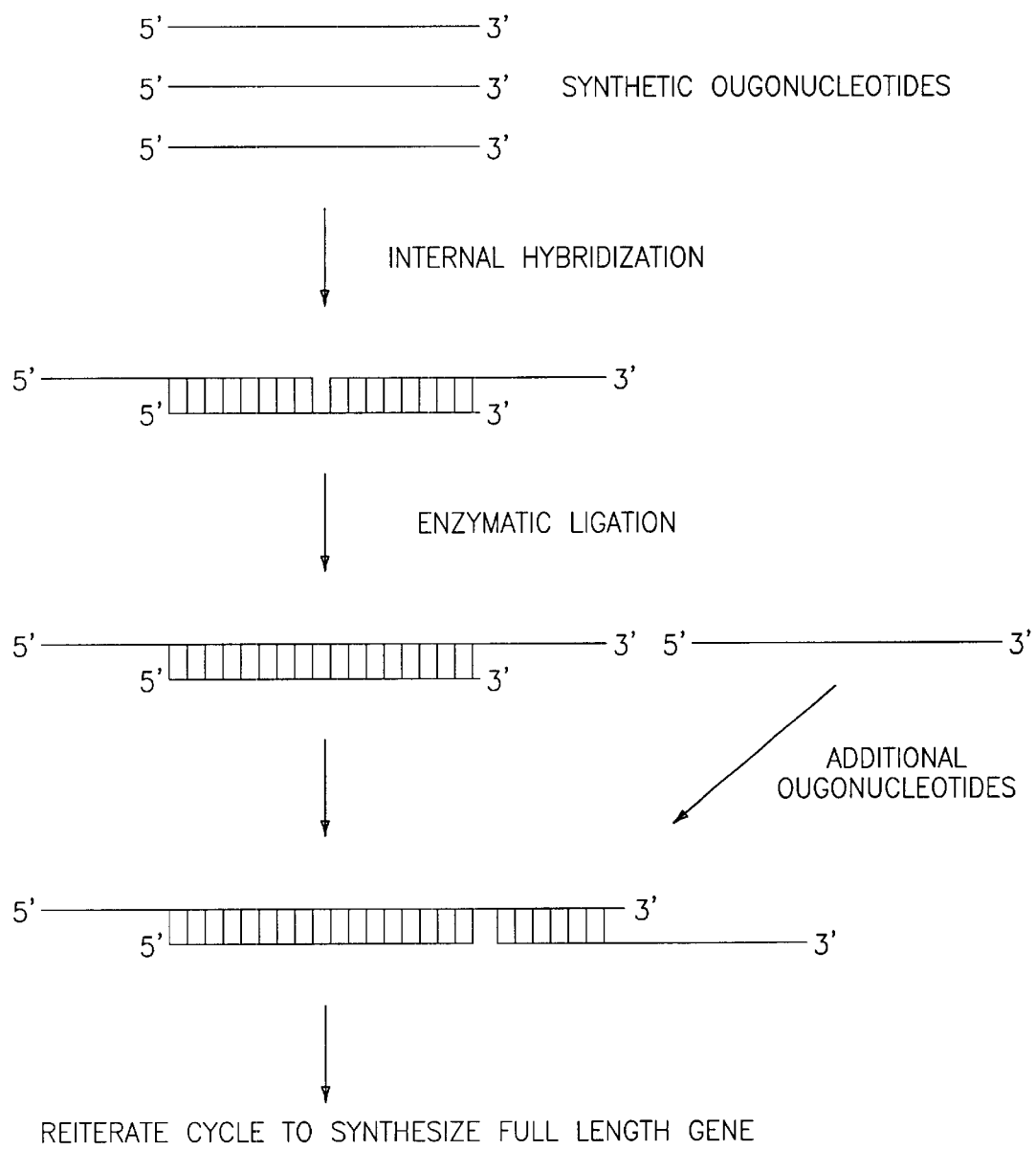
FIG. 3 is a schematic of the generation of a template for in vitro translation.

Reference is made in the specification to various methodologies known to those of skill in the art. Publications and other materials setting forth such known methodologies to which reference is made are incorporated herein by reference in their entireties as though set forth in full.

Reagents and the like to which reference is made in the following description and examples are obtainable from commercial sources, unless otherwise noted.

The present invention allows, for the first time, exquisitely precise control over the sequential arrangement of poly(lactide-co-glycolide). One important consequence of this is to allow the design of greatly improved biocompatible and absorbable medical devices. This advantage follows from the ability, previously unknown in this art, to precisely and reproducibly control the rate of hydrolysis of the copolymer.

Those of skill will appreciate that the rate of hydrolysis of a glycolic acid-glycolic bond is greater than the rate of hydrolysis of lactic acid-glycolic acid bond which is greater than the rate of hydrolysis of a glycolic acid-lactic acid bond which is greater than the rate of hydrolysis of a lactic acid-lactic acid bond. Thus, in the copolymer segment:

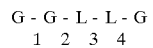

wherein glycolide is oriented to provide a hydroxy terminus on the left-most portion of the segment, i.e., HOCH2CO2CH2 . . . COOH, the order of hydrolysis is 1>4>2>3, i.e., 1 is fastest and 3 is slowest. Therefore, an engineered arrangement of sequential units by means of the present invention will allow precise control over the rate at which a copolymer produced according to the methods of the invention hydrolyzes.

Polyesters having predetermined primary sequence made in accordance with the present invention are suitable for use in a variety of applications. By varying the sequence and length of the polymer, the physical and chemical properties of the polymers can be engineered to meet predefined specifications.

The speed with which a sequential polyester degrades in an environment is based, in part, upon the rate of hydrolysis of ester bonds in the polymer chain. The present invention allows the rate of hydrolysis to be tailored in predictable fashion based upon sequence. Indeed, the precise nature of the copolymers produced according to the present invention allows, inter alia, the rate of hydrolysis to be more predictable than possible for prior random copolymers. For example, by means of the present invention, the end portions of a sequential copolymer now may be engineered to hydrolyze more quickly than the central portion of the copolymer chain.

In accordance with the present invention, thermoplastic elastomers may be constructed. Thermoplastic elastomers are multiphase compositions in which the phases are intimately dispersed. The present invention allows thermoplastic elastomers to be constructed by sequential addition of appropriate monomers to form hard and soft segments within the polymer. In addition, the polymers of the present invention may be combined with conventional polymers known to provide soft segments (such as, for example, polymers formed from epsilon caprolactone, trimethylene carbonate, dioxanone or combinations thereof) or with conventional polymers known to provide hard segments (such as, for example, homopolymeric segments of glycolic or lactic acid).

Sequential polyesters according to the present invention also allow more crystalline structures to be produced. Exquisite control over the chain sequence allows steric regularity to be achieved. Thus, while prior poly(lactide-co-glycolide) polymers containing 25 to 75 mole percent glycolide are amorphous, copolymers containing between 25 to 75 mole percent glycolide can be made crystalline.

In this manner, the tensile strength and other physical properties now can be regulated to a high degree. For example, by varying the proportion of crystalline region to amorphous region, properties such as tensile strength and brittleness now may be infinitely varied to suit particular applications.

In accordance with the present invention, oligomers of sequential polyesters may be coupled to prepare larger, higher molecular weight chains of sequential polyesters. This may be accomplished, for example, by bulk polymerization of pentachlorophenol ester monomers. An inert matrix such as CELITE™ diatomaceous earth may be used to enhance removal of the pentachlorophenol during thermal polymerization in vacuum and lead to higher yields and molecular weights. A p-nitrophenol ester may also be used to promote bulk polymerization.

Polyesters having predetermined primary sequence produced in accordance with the present invention may be used to make block copolymers. For example, two or more polymers prepared in accordance with the present invention may be used as the blocks and joined to form a block copolymer having highly uniform characteristics. Alternatively, one or more polymers prepared in accordance with the present invention may be combined with the polymers prepared by other techniques to form block copolymers or a polymer which has a biosynthetically prepared polyester of predetermined monomeric sequence as a segment thereof. In addition, polymers prepared in accordance with the present invention may be blended with each other or with polymers prepared by other techniques to provide a composition having desired characteristics. Methods of forming block copolymers, blends thereof, and blends of different polymers are well known in the art.

Useful products made from oligomeric or polymeric polymers of the present invention include fibrous surgical articles such as sutures, prosthetic ligaments, prosthetic is tendons, woven mesh, gauze, dressings, growth matrices and the like. Such fibrous surgical articles may be engineered to be made more or less elastic depending upon end use. Portions of a single length of monofilament can be made to hydrolyze at different rates and to be more or less elastic than other portions.

In one presently preferred mode, the polymers of the invention are used to make surgical sutures. The principles applied in designing and constructing sutures are known in the art and are set forth herein in summary form and by reference to known publications. Those of skill will recognize that many of these principles will apply also to the design and construction of other medical devices which may be produced using the polymers of the invention.

Multifilament sutures of the present invention may be made by methods known in the art. Braid constructions such as those disclosed and claimed in U.S. Pat. Nos. 5,059,213 and 5,019,093 are suitable for the polyester multifilament suture of the present invention.

Monofilament sutures may be manufactured by methods well known in the art. A suitable process for the manufacture of monofilament sutures of the present invention comprises the operations of melt extruding the polyester resin to provide a monofilament, and stretching the solidified monofilament at a temperature above ambient temperature in water (or other suitable liquid medium) or in air (or other suitable gaseous medium) to provide a stretched monofilament. Optionally, the monofilament may then be annealed to provide the finished suture.

FIG. 1A schematically illustrates a monofilament suture manufacturing operation which is especially suitable for producing larger size sutures, e.g., those of sizes 3/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resin prepared in accordance with the present invention are introduced to the extruder through hopper 12. Any of the polyester compositions of the present invention which are useful for the formation of fibers can be used herein.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e. the air gap, can vary and can advantageously be from about 0.5 to about 100 cm. If desired, a chimney (not shown), or shield, can be provided to reduce the length of the air gap, e.g. to from 1 to 10 cm, thereby isolating monofilament 16 from contact with air currents which might otherwise affect the cooling of the monofilament in an unpredictable manner.

Monofilament 16 is passed through quench bath 17 around driven roller 18 and over idle rollers 19 and 20.

Optionally, a wiper (not shown) may remove excess water from the monofilament as it is removed from quench bath 17. On exiting the quench bath the monofilament is wrapped around a first godet 21 provided with nip roll 22 to prevent slippage which might otherwise result from the subsequent stretching operation. Monofilament 16 passing from godet 21 is stretched, to effect its orientation and thereby increase its tensile strength. In the stretching operation shown in FIG. 1A, generally suitable for larger size sutures, e.g., sizes 2 to 3/0, monfilament 16 is drawn through hot water draw bath 23 by means of second godet 24 which rotates at a higher speed than first godet 21 to provide the desired stretch ratio.

In an alternate stretching operation shown in FIG. 1B, generally preferred for smaller suture sizes, e.g., sizes 4/0 to 8/0, monofilament 16 is drawn by second godet 24' through hot air convection oven chamber 23' to provide the desired amount of stretch. Following the stretching operation shown in FIGS. 1A or 1B, monofilament 16 optionally may be subjected to an on-line annealing without shrinkage or relaxation with shrinkage operation as a result of which the monofilament shrinks. In the process of FIGS. 1A and 1B, on-line annealing with or without relaxation when desired is accomplished by driving monofilament 16 by third godet 26 through second hot air oven chamber 25. For relaxation, the third godet rotates at a slower speed than the second godet thus relieving tension on the filament.

Although not depicted in the Figures, those of skill will appreciate that multiple stretching steps may be used, as are known in the art.

A suture in accordance with the present invention, suture 101, may be attached to a surgical needle 100 as shown in FIG. 2 by methods well known in the art. Wounds may be sutured by approximating tissue and passing the needled suture through tissue to create wound closure. The needle preferably is then removed from the suture and the suture tied.

Those of skill will appreciate that other medical articles or devices can be manufactured from the sequential polyesters of the present invention. These include, but are not limited to, solid products, which may be molded or machined, such as orthopedic pins, clamps, screws and plates; clips; staples; hooks; buttons; snaps; bone substitutes such as mandible prostheses; needles; non-permanent intrauterine devices such as spermicides; temporary draining or testing tubes or capillaries; surgical instruments; vascular and ocular implants or supports; vertebral discs; and extracorporeal tubing for, e.g., kidney and heart-lung machines. Also included are fibrillar products, knitted or woven, and including velours, such as burn dressings; hernia patches; absorbent paper or swabs; medicated dressings; facial substitutes; gauze, fabric, sheet, felt or sponge for hemostasis, as, e.g., of the liver or other internal organs; gauze bandages; and dental packs. Other products include flake or powder for burns or abrasions; foam as an absorbable prosthesis; wire substitutes in fixations; and film sprays for prosthetic devices. The sequential polyesters of the present invention may be used alone or in combination with other materials to produce products including those listed hereinabove, as well as combination products such as digestible ion-exchange resins; digestible or time-release devices and drug delivery devices or systems such as pills, patches and pellets; reinforced bone pins, needles, and the like; arterial grafts or substitutes; bandages for skin surfaces; and burn dressings (e.g., in combination with other polymeric films). Nonabsorbable sutures and methods of making them are well known and are described, for example, in U.S. Pat. Nos. 3,630,205 and 4,911,165. The biocompatible sequential polyesters of the present invention thus may be combined or blended with the polypropylene compositions of those patents to produce medical articles such as sutures. Presently preferred medical articles include sutures as set forth above, as well as absorbable staples and clips as set forth, for example, in U.S. Pat. Nos. 4,523,591, 4,744,365, 4,839,130, 4,844,854, and 5,124,103. These and other non-limiting useful medical articles are known in the art and contemplated as within the scope of the present invention.

Implantable surgical articles made from the polyesters of this invention may be designed to be implanted into patients where the articles are hydrolyzed and absorbed.

It is contemplated that it may be desirable to dye the medical articles of the present invention. For example, a dye may be used to increase visibility of a suture in the surgical field. Dyes known to be suitable for incorporation into medical articles can be used alone or in combination to produce a desired color or shade. Such dyes include but are not limited to Logwood extract, carbon black, and D & C Green No. 6 as described in Marrion, D. M., *U.S. Colorants for Food, Drugs, and Cosmetics* (1979). Preferably, medical articles such as sutures in accordance with the invention are dyed by adding up to about a few percent dye, such as D & C Green No. 6, to the resin prior to extrusion. Those of skill who appreciate the teachings of the present invention will recognize that detectable moieties also may be incorporated directly into the polymer itself, e.g., via a side chain linkage. Such detectable moieties include, but are not limited to, dyes, fluorescers, bioluminescent and chemiluminescent molecules, radionuclides and the like.

Drug delivery devices or systems, as used herein, include any device or article of manufacture which is used to deliver a medicinal agent. The term "medicinal agent" is used in its broadest sense and includes any substance or mixture of substances useful in medicine. Thus, it is understood that a medicinal agent may be a drug, enzyme, peptide, protein, dye, or diagnostic agent such as a detectable moiety which may have no biological activity per se.

Examples of various medicinals that can be used in accordance with the present invention include antimicrobials, analgesics, antipyretics, anesthetics, antiepileptics, antihistamines, anti-inflammatories, cardiovascular drugs, diagnostic agents, sympathomimetics, cholinomimetics, anti-muscarinics, antispasmodics, hormones, growth factors, muscle relaxants, adrenergic neuron blockers, anti-neoplastics, immunosuppressants, gastrointestinal drugs, diuretics, steroids and enzymes. It is also intended that combinations of medicinals can be used in accordance with the present invention.

Standard reference works setting forth the general principles of recombinant DNA technology include Watson, J. D. et al., *Molecular Biology of the Gene*, Volumes I and II, The Benjamin/Cummings Publishing Company, Inc., publisher, Menlo Park, Calif. (1987); Darnell, J. E. et al., *Molecular Cell Biology*, Scientific American Books, Inc., publisher, New York, N.Y. (1986); Lewin, B. M., *Genes II*, John Wiley & Sons, publishers, New York, N.Y. (1985); Old, R. W., et al., *Principles of Gene Manipulation: An Introduction to Genetic Engineering*, 2d edition, University of California Press, publisher, Berkeley, Calif. (1981); and Maniatis, T., et al., *Molecular Cloning: A Laboratory Manual*, Cold Spring Harbor Laboratory, publisher, Cold Spring Harbor, N.Y. (1982).

It may be convenient in understanding the invention to set forth definitions of certain terms used herein.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "vector" is meant a DNA molecule, derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible. Thus, by "DNA expression vector" is meant any autonomous element capable of replicating in a host independently of the host's chromosome, after additional sequences of DNA have been incorporated into the autonomous element's genome. Such DNA expression vectors include bacterial plasmids and phages. Preferred for the purposes of the present invention is the lambda gtII expression vector. Also preferred is the commercially available pSPORT plasmid (BRL, Gaithersburg, Md.).

A nucleotide sequence encoding the polyesters of the invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis, T., et al., supra, and are known in the art.

A nucleic acid molecule, such as DNA, is said to be "capable of expressing" a polyester if it contains nucleotide sequences which contain transcriptional and translational regulatory information and such sequences are "operably linked" to nucleotide sequences which encode the polyester. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of polyester synthesis. Such regions will normally include those 5'-non-coding sequences involved with initiation of transcription and translation, such as the TATA box, capping sequence, CAAT sequence, and the like.

If desired, a non-coding region 3' to the gene sequence coding for the polyester may be provided by well-known methods. This region may provide transcriptional termination regulatory sequences, such as termination and polyadenylation. Where the transcriptional termination signals are not satisfactorily functional in the expression host cell or system, a 3' region functional in the host cell may be substituted.

Two nucleotide sequences (such as a promoter region sequence and a polyester encoding sequence) are said to be operably linked if the nature of the linkage between the two sequences does not (1) result in the introduction of a frame-shift mutation, (2) interfere with the ability of the promoter region sequence to direct the transcription of the polyester encoding sequence, or (3) interfere with the ability of the polyester encoding sequence to be transcribed by the promoter region sequence. Thus, a promoter region would be operably linked to a polyester encoding sequence if the promoter were capable of effecting transcription of that sequence.

In a presently preferred embodiment, the present invention utilizes a cell-free translation system to produce polyesters, as is described more fully hereinafter. The present invention also contemplates the expression of polyesters and their functional derivatives in prokaryotic or eukaryotic cells. Preferred prokaryotic hosts include bacteria such as *E. coli, Bacillus,* Streptomyces, Pseudomonas, Salmonella, Serratia, etc. The most preferred prokaryotic host is *E. coli.*

The sequential polyester produced according to the invention may be isolated and purified by conventional methods, such as extraction, precipitation, chromatography, affinity chromatography, electrophoresis, or the like.

In one embodiment, the present invention is directed to the use of synthetic messenger ribonucleic acid (mRNA) as a template for the synthesis of defined sequences of lactic acid and glycolic acid copolymers.

mRNA prepared according to the methods of the invention and known in the art can be used to direct defined copolymer synthesis in a cell-free in vitro translation system. In vitro translation systems are well known in the art, and their use for the incorporation of unnatural amino acids into proteins is described, for example, by Noren, et al., *Science* 244:182 (1989); Robertson, et al., *Nucleic Acids Res.* 17(23):9649 (1989); Anthony-Cahill, et al., *TIBS* [VOL]:400 (1989); Robertson, et al., *J. Am. Chem. Soc.* 113:2722 (1991); Mendel, et al., *J. Am. Chem. Soc.* 133:2758 (1991); and Ellman, et al., *Science* 225:197 (1992), the disclosures of which are incorporated herein in full. Thus, for example, transfer RNA (tRNA) can be chemically modified by known methods to carry lactate rather then the cognate amino acid. When the appropriate codon is reached during translation of mRNA, the tRNA-lactate molecule binds to that codon. Therefore, through the specific synthesis of tRNA's for both lactate and glycolate, a cell free system, programmed by a synthetic mRNA, can be used according to the present invention to synthesize copolymer of lactate and glycolate as defined sequences.

In a preferred embodiment of the invention, chemical acylation may proceed with the generation of truncated tRNA that recognize stop codons, and are therefore termed herein "suppressor tRNA" (abbreviated "Sup-tRNA"). Sup-tRNA generally will lack the two 3' nucleotides: CpA. In separate reactions, CpA may be acylated with the nonamino acid (X), employing well known acylation methods. The resulting CpA-X may then be enzymatically ligated onto the Sup-tRNA to generate the mature tRNA: Sup-tRNA-X. An RNA template may be generated that has the appropriate stop codon within the open reading frame that matches the anticodon in the Sup-tRNA-X. An in vitro translation system may be used, such that X is incorporated at the template directed site.

Truncated tRNA molecules may be synthesized by known methods, for example, by employing modifications of the methods described by Noren, et al., (1989), Robertson, et al., (1991), and Ellman, et al., (1992), incorporated herein in full. In a preferred embodiment, the gene for yeast tRNA$^{phe}$ may be cloned into a M13 type phage vector using well known cloning methods. The anticodon loop may be altered to recognize stop codons using methods well known in the art, such as, for example, oligonucleotide site directed mutagenesis. Since there are three stop codons in the genetic code, two may be used to encode lactate and glycolate, and the third is reserved for the actual translation stop codon. In a presently preferred embodiment, UAA encodes lactate, and UAG encodes glycolate. The remaining stop codon, UGA, may be used for translation termination.

Those of skill will recognize that it may be desirable to truncate the two 3' nucleotides (CpA) of the tRNA$^{phe}$, using well known methods, such as mutagenesis as described herein and as well known in the art. The gene for the truncated Sup-tRNA$^{phe}$ may be cloned by known methods into an appropriate vector downstream of a suitable promoter. Examples of suitable promoters according to the invention include the T7 or T4 RNA polymerase promoters. An in vitro transcription reaction as described herein may be used to generate workable quantities of the truncated Sup-tRNA$^{phe}$.

The CpA dinucleotide may be synthesized according to the present invention in large quantities employing known methods. Presently preferred is the use of a solid phase Automated DNA synthesizer according to methods known in the art. Chemical acylation of the dinucleotide CpA may be performed by known methods. Presently preferred is the method of Noren, et al. (1989) supra. Briefly, the exocyclic amine of Cytidine is protected with ortho-nitrophenylsulfenyl chloride (NPS-CL). Since there is no reactive amine on either glycolate or lactate, there is no need for any protection reactions. Glycolate and lactate are coupled to the 2' or 3' hydroxyl group of the Adenine (the 2' and 3' acylations rapidly interconvert). The coupling reaction is carried out with N,N'-carbonyldimidazole as an activating reagent. After the coupling reaction the NPS protecting groups on the Cytidine are removed with aqueous thiosulfate. The result is CpA-lactate and CpA-glycolate.

Purified CpA-lactate and CpA-glycolate may be ligated onto Sup-tRNA$_{phe}$ employing well known methods, such as, for example, by the use of the enzyme T4-RNA ligase. The resulting Sup-tRNA$^{phe}$-lactate and Sup-tRNA$^{phe}$-glycolate may be purified by any known methods, including but not limited to column chromatography.

The template for the in vitro translation system according to the present invention may be synthesized from oligonucleotides. Oligonucleotides of defined sequences may be synthesized by known methods including, but not limited to, automated DNA synthesis. A scheme of overlapping internal hybridizations may be used to generate a complete template, as depicted in FIG. 3. In one embodiment, the template may be ligated by known methods into an appropriate vector downstream from and in frame with a protein coding segment. The purpose of the peptide segment in this presently preferred embodiment is to efficiently initiate translation. The junction between the amide and polyester segment will be chosen to permit rapid, efficient, and specific post-translational cleavage of the polyester segment from the amide leader segment. Non-limiting examples of possible amide-polyester junctions according to the invention include amide regions terminating with: 1) methionine, which may be cleaved with cyanogen bromide, 2) lysine or arginine, which may be cleaved with trypsin, 3) phenylalanine, tryptophan or tyrosine, which may be cleaved by chymotrypsin.

Figure 4:
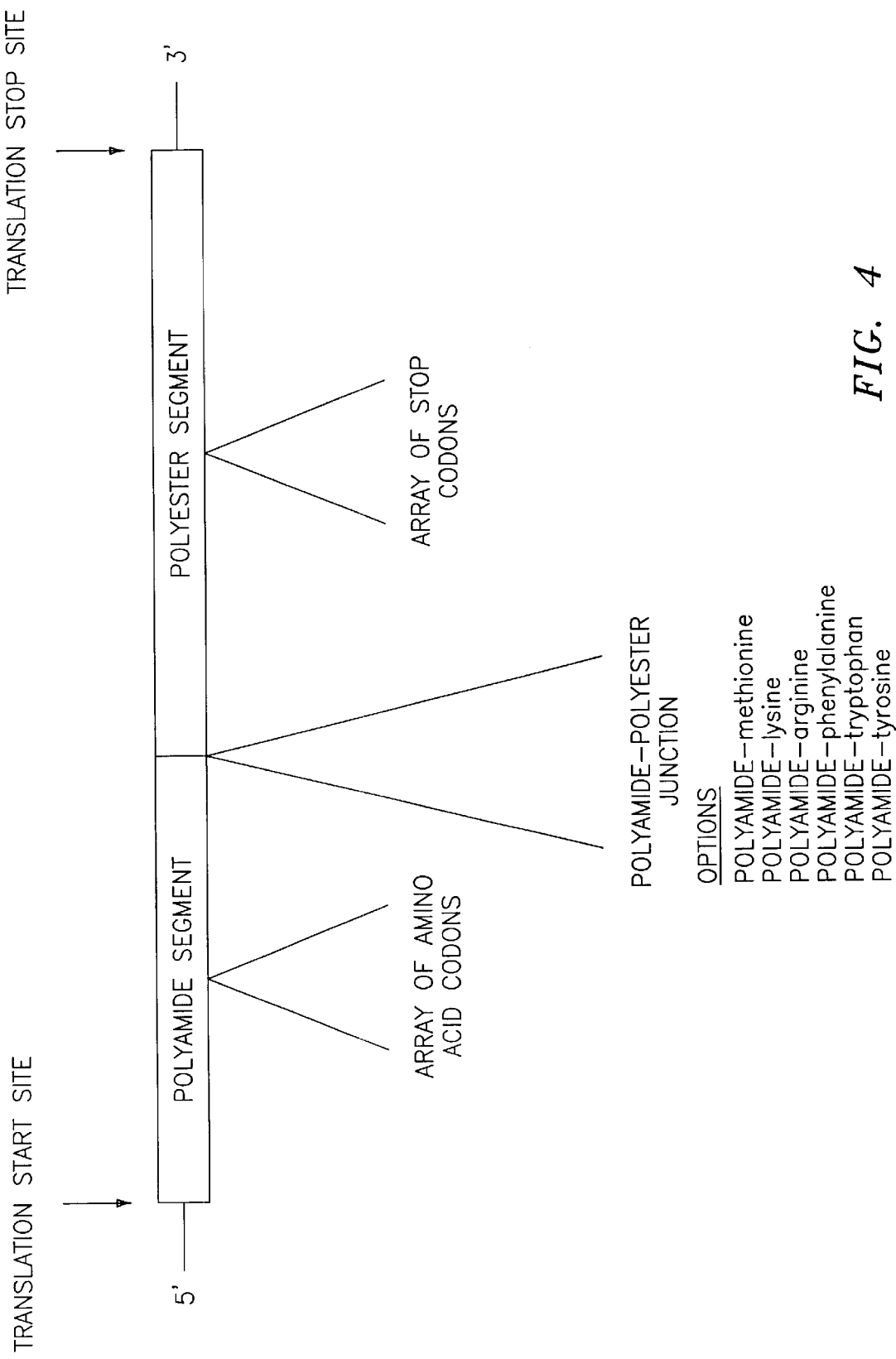
FIG. 4 is a schematic showing the general structure of a template for in vitro translation.

In a preferred embodiment, the sequence of the polyester-encoding template is a series of stop codons recognized by Sup-tRNA$^{phe}$-glycolate. According to this embodiment, a string of UAA and UAG units will encode the corresponding sequence of lactate and glycolate units. Those of skill having benefit of the teachings of the present specification will recognize that any combination of triplet codons may be chosen to define any ordered sequence of lactate and glycolate units. At the completion of the sequence, the stop codon UAG, which in the presently preferred embodiment is not suppressed, is used to terminate translation. Thus, the template so produced according to the invention will have the general structure shown in FIG. 4.

In a preferred embodiment of the invention, an *E. coli* in vitro translation system may be employed. *E. coli* aminoacyl tRNA transferase cannot amino-acylate yeast tRNA, which, as described above, can be the origin of the Sup-tRNA$^{phe}$-glycolate. Thus, it will be appreciated that once the Sup-tRNAphe-lactate and Sup-tRNAphe-glycolate participate in a translation cycle, the free Sup-tRNA$^{phe}$ will not be amino-acylated with phenylalanine and thus interfere with polyester synthesis. In addition, the *E. coli* strain used to generate the in vitro translation extract is a recombinant strain that does not express tRNA for the two stop codons used to encode glycolate and lactate. Therefore, native tRNA will not compete with Sup-tRNA$^{phe}$-glycolate for recognition of stop codons.

The translation extract may be used according to the invention to synthesize polymers in conjunction with the artificial template. Thus, for example, free amino acids, ATP, GTP, Sup-tRNA$^{phe}$-lactate and Sup-tRNA$^{phe}$-glycolate, and template may be added to the *E. coli* extract in order to allow translation to occur. Translation may be terminated by any appropriate means as are well known in the art, for example, by the addition of a detergent.

As used herein, "Releasing Factors" are proteins necessary to terminate translation at stop codons. Two of these factors are designated RF 1 (which recognizes UAA and UAG) and RF 2 (which recognizes UAA and UGA). In a preferred embodiment of the invention, an *E. coli* translation system may be employed based upon RF mutants such that competition between chain extension and termination is minimized. Since the Releasing Factors have UAA in common, it is presently preferred to make the *E. coli* cell-free translation system from *E. coli* that do not express RF 1. By so doing, competition for the termination of translation at UAG codons may be prevented or minimized.

The amide-polyester polymer may be purified by known methods, such as, for example, column chromatography and phase separative procedures. The purified polymer may be processed by cleavage steps such as those described herein to separate the amide from the polyester segment. If desired, the polyester segment may be further purified by methods known in the art, such as extraction methods or additional column chromatography.

Methods by which tRNA$^{phe}$-phenylalanine may be deaminated to tRNA$^{phe}$-phenyllactyl are known and are described, for example, by Fahnestock and Rich, *Science* 173:340 (1971). The resulting a-hydroxyael analog of tRNA$^{phe}$-phenylalanine has been shown to be active in an in vitro translation system to generate polyesters. In a presently preferred embodiment of the invention, this strategy may be applied to the production of Sup-tRNA-lactate and Sup-tRNA-glycolate. Instead of generating Sup-tRNA by an in vitro transcription system, and then ligating CpA-lactate or CpA-glycolate to the tRNA, Sup-tRNA$^{gly}$-glycolate and Sup-tRNA$^{ala}$-lactate may be produced directly in a fermentation process. These tRNA species are then translated in vitro using templates and translation systems as described herein.

Thus, for example, genes for yeast tRNA$^{gly}$ and tRNA$^{ala}$ may be cloned onto an appropriate cloning vector using methods known to those of skill. Appropriate cloning vectors may be obtained from commercial sources, and include, for example, the M13 type phage vector. Once the genes have been inserted into the cloning vector, new anticodons that recognize stop codons (Sup-tRNA$^{gly}$ and Sup-tRNA$^{ala}$) may be inserted by known methods, such as, for example, site directed mutagenesis. The resulting mutagenized tRNA will thus contain new anticodons that recognize stop codons (Sup-tRNA$^{gly}$ and Sup-tRNA$^{ala}$). In a presently preferred embodiment, the stop codons for tRNA$^{ala}$ and for tRNA$^{gly}$ may be UAA and UAG, respectively. The new tRNA genes may be cloned onto an appropriate expression vector using known methods. Preferably, the new tRNA genes will be cloned onto the chosen expression vector downstream of an appropriate promoter. In a preferred embodiment, the promoter will be an inducible promoter. The resulting expression vector or plasmid may be used to transform an appropriate host cell, such as, for example, yeast. The resulting recombinant yeast strain will be capable of producing quantities of Sup-tRNA$^{gly}$-glycine and Sup-tRNA$^{ala}$-alanine.

Thus, in a preferred embodiment, the cultures of the recombinant yeast cells may be grown to near confluence employing known culture methods. If necessary or desirable, a protein synthesis inhibitor may be added and the inducible tRNA genes activated. The yeast will then express the tRNA$^{gly}$ and tRNA$^{ala}$, which are aminoacylated with the appropriate amino acid. The resulting Sup-tRNA$^{gly}$-glycine and Sup-tRNA$^{ala}$-alanine may be purified by standard techniques.

Figure 5:
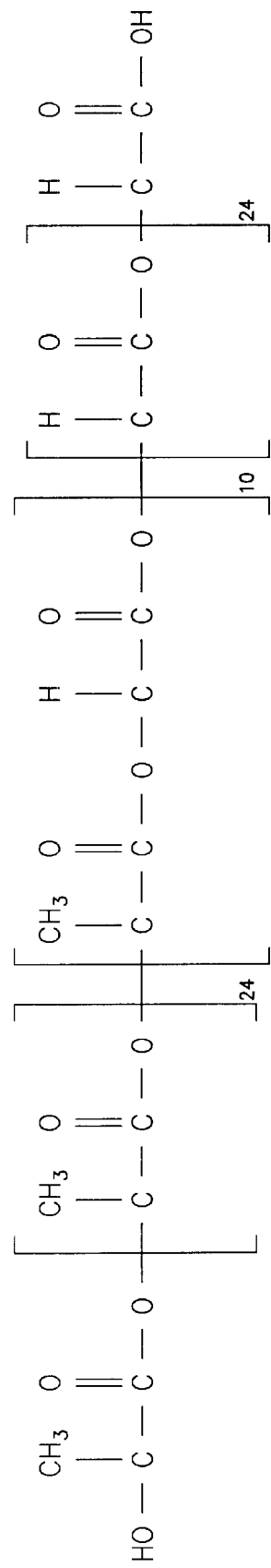
FIG. 5 illustrates the deamination of tRNA-alanine and tRNA-glycine to their respective a-hydroxyael analogs.

After purification, the Sup-tRNA$^{gly}$-glycine and Sup-tRNA$^{ala}$-alanine may be deaminated by known methods, such as described, for example, by Fahnestock and Rich (1971) (supra). Thus, according to this presently preferred method, purified Sup-tRNA$^{gly}$-glycine and Sup-tRNA$^{ala}$-alanine are incubated in 0.25 M sodium acetate, 0.01 M magnesium acetate, 1M NaNO$_2$ at 24° C. The pH is maintained at pH 4.3 with acetic acid. These reaction conditions result in the deamination of the amino acids on the tRNA to the a-hydroxyael analogs, as shown in FIG. 5. The resulting Sup-tRNAgly-glycolate and Sup-tRNA$^{ala}$-lactate may be purified by known methods, such as, for example, column chromatography.

The initiator codon for translation will be selected by the skilled artisan based upon known initiation principles and an appreciation of the teachings of the present invention. For example, polyester synthesis may be initiated by a native E. coli MET-tRNAf. In this case, the resulting polyester has a methionine as the first residue. This first methionine may, if desired, be deleted from the polyester by known methods.

In a presently preferred embodiment, a synthetic initiator tRNA may be synthesized that recognizes the AUG codon, but carries a lactate instead of methionine. A truncated version of the tRNAf may be generated that does not have the CpA dinucleotide at the 3' termini. A synthetic CpA dinucleotide may be synthesized and coupled with lactate to form CpA-lactate. The CpA-lactate may be ligated onto the 3' termini of the truncated tRNAf. The resulting Lactate-tRNAf initiates translation by recognizing the AUG codon. Thus, translation is initiated with lactate rather than methionine. Those of skill will appreciate that where, for example, an E. coli in vitro translation system is to be used, the starting tRNAf must be E. coli so that the initiation factors in the E. coli in vitro translation system will recognize it.

The invention also relates to nucleotide sequences which encode a fusion product or chimera comprising a polyester or fragment thereof and a detectable enzyme such as beta-galactosidase, or any desired homologous or heterologous protein or peptide. Methods for producing fusion proteins are taught, for example, Bai, D. H., et al., *J. Biol. Chem.* 261:12395–12399 (1986), or Huynh, T. U., et al., "Construction and Screening cDNA Libraries in lambda-gt10 and lambda-gt11," in *DNA Cloning Techniques: A Practical Approach*, D. Glover (ed.), IRL Press, Oxford, 1985, pp. 49–77.

The polyester, functional derivative thereof, or fusion protein comprising polyester or fragment thereof and a detectable enzyme or desired protein or peptide may be isolated according to conventional methods known to those skilled in the art. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immuno-precipitation.

Preferred cell free systems of the invention will be derived from E. coli, which is well characterized and which is thus a convenient model. The choice of other prokaryotic and eukaryotic derived cell free systems will be routinely made by those of skill.

Where an E. coli derived cell free system is employed according to the invention, yeast tRNA molecules would be chosen since it has been demonstrated that yeast tRNA's are not recognized by E. coli amino acyl tRNA synthetases (the enzymes in the cell free system that will charge tRNA's with the cognate amino acids). Thus, if an E. coli cell free protein synthesis system is used with yeast tRNA's, the yeast tRNA's would not be charged with any amino acids, such that polymer synthesis would proceed without interference.

Alteration of the yeast tRNA molecules to carry modified lactic acid and glycolic acid is carried out by routine chemical methods, such that the 5' phosphate terminus is shortened by two ribonucleotides. In native tRNA, the two nucleotides are always CpA.

In a separate reaction, a ribonucleotide dimer, CpA, would be chemically modified such that a lactate or glycolate is covalently attached to the ribose moiety at the 2' position of the A ribonucleotide. The resulting CpA-Lactate and CpA-Glycolate products are then enzymatically linked to appropriate tRNA molecules through the use of T4 RNA ligase.

The mRNA used to program the cell free system according to the invention may consist of repeating units of two triplet codons. One codon is recognized by tRNA-Lactate and the other by tRNA-Glycolate. The order of the codons in the mRNA determines the order of the lactate and glycolate units. Since initiation of the synthetic pathway is a complex process which involves a series of reactions centered on a specific start codon, it may be necessary or desirable to start copolymer synthesis with a short segment of mRNA sequence that codes for polypeptide. Once translation is initiated, and a short segment of polypeptide is produced, the ribosome will reach the beginning of the lactate and glycolate codons. Thus, a chimeric polymer will be generated consisting of a short polyamide section, contiguous with a larger polyester segment. By incorporating a methionine at the end of the polyamide section, the polyester can be liberated by treatment of the copolymer with cyanogen bromide, which specifically cleaves polyamides at the carboxyl side of methionines, as is known in the art.

In another method according to the present invention, longer ribonucleotides, consisting of the first 10 or so bases of the tRNA from the 5' terminus, are covalently linked by known methods to lactate or glycolate. In native tRNAs this 10 base region base-pairs with corresponding ribonucleotides, forming an RNA-RNA duplex. The resulting product consists of lactate and glycolate oligoribonucleotides. Mature tRNA's are generated by hydrogen bonding of the lactate and glycolate oligoribonucleotides to the matching bases on the tRNA's. This manipulation bypasses the ligation step described above catalyzed by T4 RNA ligase.

In a cell free system according to this embodiment, excess lactate or glycolate oligoribonucleotides are reacted with a limiting concentration of precursor tRNA molecules. During the course of the translation reaction, the temperature is cycled such that at low temperature the lactate or glycolate-oligoribonucleotides anneal to the precursor tRNA's and participate in polymer chain elongation. At high temperatures, the base pairing between the oligoribonucleotides (that have given up the lactate or glcolate) and the precursor tRNA's is disrupted, such that when the temperature is cycled down, unused lactate or glycolate-oligoribonucleotides anneal to the precursor tRNA's.

The plasmid with the template may be used to drive an in vitro transcription reaction to produce mRNA. The resulting mRNA may be purified by column chromatography, and used as the template for in vitro translation.

Having now described the invention, the same will be more fully understood by those of skill with reference to the following non-limiting examples.

EXAMPLE I

Template Directed Synthesis of a Polyester without a Polypeptide Leader Sequence I) Designation of Polyester Sequence The synthetic method of the present invention allows synthesis of polyesters derived from the a-amino acid analogues of any of the amino acids with the exception of proline. There are three STOP codons: UAA; UAG; and UGA. In the present example, one of these STOP codons is reserved for the STOP signal for the polyester. The remaining two STOP codons thus are available for encoding the monomer units of the polyester. In the present example, lactate and glycolate are encoded by UAA and UAG, respectively. The methods of the invention are utilized to construct a polyester having the following defined sequence:

$$[\text{Lactate}]_{25}\text{-}[\text{Lactate-Glycolate}]_{10}\text{-}[\text{Glycolate}]_{25} \qquad \text{I}$$

The chemical structure of I is shown in FIG. 6.
II) Design and Synthesis of Synthetic Gene
A) The polyester coding region The template sequence for the polyester having sequence I is the sequence of the corresponding codons for each monomer in the polyester chain. Initiation of translation always occurs at an AUG codon. Therefore, the first lactate in the polyester chain is encoded by an AUG codon. This is accomplished through the use of a specially synthesized Met-tRNAf modified to carry lactate instead of methionine, as described herein. Alternatively, a methionine is incorporated in the first position of the polymer chain. The resulting polymer is treated with cyanogen bromide to remove the methionine, as described herein.

In the present example, the template is synthesized such that the first AUG codon encodes a lactate. Thus, the template, which encodes a polyester having the sequence I, has the following sequence:

$$5'\text{-AUG-}[\text{UAA}]_{24}\text{-}[\text{UAA-UAG}]_{10}\text{-}[\text{UAG}]_{25}\text{-UGA-}3' \qquad \text{II}$$

Alternatively, if the template is designed such that the first codon is used to encode a methionine, then the template is constructed as follows:

$$5'\text{-AUG-}[\text{UAA}]_{25}\text{-}[\text{UAA-UAG}]_{10}\text{-}[\text{UAG}]_{25}\text{-UGA-}3' \qquad \text{III}$$

B) Stepwise Construction of the Transcriptional Unit

1) Construction of the initiator region of the synthetic gene: Since in vitro translation of the synthetic mRNA is carried out in an *E. coli* cell free system, the initiator region must be recognized by *E. coli* ribosomes. In this example, the initiator region is identical to the *E. coli* trpA gene. Oligonucleotides of the following sequence are synthesized:

5'C-AGC-ACG-AGG-GGA-AAT-CTG-ATGTAAT-GCATG3'

3'-TGCAG-TCG-TGC-TCC-CCT-TTA-GAC-TACATTA-C-5'  IV

Key
Bold=start codon
Underline=trpA initiator sequence
Plain text=Sph I adaptors
Italics=Aat II adaptors The oligonucleotides are combined, heated to 90° C., then allowed to cool slowly to room temperature. During cooling, the oligonucleotides anneal to form a double stranded DNA.

Oligonucleotide IV is ligated into the commercially available pSPORT I plasmid (BRL, Gaithersburg, Md.) that has been cleaved with the Aat II and Sph I restriction endonucleases.

1) Aat II Digestion of pSPORT I Plasmid

A 5 mg sample of pSPORT I DNA is treated with 10 units of Aat II (New England Biolabs) for 60 minutes at 37° C. in a 50 ml reaction consisting of 50 mM Kacetate, 20 mM Tris-acetate (pH 7.9), 10 mM MgAcetate, 1 mM dithiothreitol (DTT) and 100 mg/ml bovine serum albumin (BSA). The reaction is terminated with the addition of 150 ml 10 mM Tris-HCl (pH 8.0), 1 mM EDTA, followed by extraction with an equal volume of 1:1 buffer saturated phenol:chloroform, isoamyl alcohol (24:1). The aqueous phase is collected, and precipitated by the addition of 20 ml 3 M sodium acetate (pH 5.2) and 400 ml absolute ethanol. The precipitated DNA is collected by centrifugation, washed once in 70% ethanol, then resuspended in 10 ml of water.

2) Sph I Digestion of pSPORT I Plasmid

A 5 mg sample of the Aat II digested pSPORT I DNA is treated with 10 units of Sph I (New England Biolabs) for 60 minutes at 37° C. in a 50 ml reaction consisting of 50 mM NaCl, 10 mM Tris-HCl (pH 7.9), 1 mM DTT and 100 mg/ml BSA. The reaction is terminated with the addition of 150 ml 10 mM Tris-HCl (pH 8.0), 1 mM EDTA, followed by extraction with an equal volume of 1:1 buffer saturated phenol:chloroform, isoamyl alcohol (24:1). The aqueous phase is collected, and precipitated by the addition of 20 ml 3 M sodium acetate (pH 5.2) and 400 ml absolute ethanol. The precipitated DNA is collected by centrifugation, washed once in 70% ethanol, then resuspended in 10 ml of water.

3) Ligation of Oligonucleotide IV into Aat II and Sph I Digested pSPORT I Plasmid The Aat II and Sph I digested pSPORT I plasmid is combined with 1 mg of annealed oligonucleotide IV. The DNA solution is treated with 10 units of T4 DNA ligase in a 100 ml reaction consisting of 50 mM Tris-HCl (pH 7.8), 10 mM DTT, 1 mM ATP and 100 mg/ml BSA at 15° C. for 16 hours. The resulting plasmid is designated pSPORT Ia.

4) Transformation and Selection of pSPORT Ia

The ligation reaction is used to transform competent *E. coli* DH5-a. The transformed *E. coli* are selected for the presence of plasmid by growing colonies on Lb agar plates with 100 mg/ml ampicilin. Ampicilin resistant colonies are recovered and grown in Lb liquid media with 100 mg/ml ampicilin. Plasmid DNA is purified from the cultures by standard miniprep procedures. The correct construct is verified by the lack of cleavage with Aat II.

5) Cleavage of pSPORT Ia with Sph I and Hind III

A 5 mg sample of pSPORT Ia is digested with Sph I as described above. The Sph I digested DNA is treated with 10 units of Hind III (New England Biolabs) for 60 minutes at 37° C. in a 50 ml reaction consisting of 50 mM NaCl, 10 mM Tris-HCl (pH 7.9), 10 mM MgCl$_2$, 1 mM DTT and 100 mg/ml BSA. The DNA is purified as described above.

6) Creation of a Fok I Site in pSPORT Ia

The pSPORT Ia plasmid is adapted so that the rest of the polyester coding sequence can be constructed downstream of, and in frame with, the ATG start codon. To accomplish this, oligonucleotides that contain a Fok I site are ligated into pSPORT Ia downstream of the ATG start codon. The following oligonucleotides are synthesized:

5'-C-<u>GCG</u>-CATCC-A-3'

3'GTACG-<u>CGC</u>-GTAGG-TTCGA-5'  V

Key
Bold=Sph I adaptors
Underline=spacer sequence
Plain text=Fok I site
Italics=Hind III adapter The oligonucleotides having the sequence V are combined, heated to 90° C., then allowed to cool slowly to room temperature. During cooling, the oligonucleotides anneal to form a double stranded DNA. The DNA is ligated into pSPORT Ia that has been cleaved with Sph I and Hind III.

7) Ligation of Oligonucleotide V into Sph I and Hind III Digested pSPORT Ia

The Sph I and Hind III digested pSPORT Ia is combined with 1 mg of annealed oligonucleotide V. The DNA solution is treated with 10 units of T4 DNA ligase in a 100 ml reaction consisting of 50 mM Tris-HCl (pH 7.8), 10 mM DTT, 1 mM ATP and 100 mg/ml BSA at 15° C. for 16 hours. The resulting plasmid is designated pSPORT Ib. The new sequence in pSPORT Ib is as follows:

-5'-AGC-ACG-AGG-GGA-AAT-CTG-ATGTAAT-GCATGC-GCG-CATCC-A-3'-

-3'-TGCAG-TCG-TGC-TCC-CCT-TTA-GAC-TACATTA-CG-TACG-CGC-GTAGG-TTCGA-5'-

Key
Bold=Fok I site

8) Transformation and Selection of pSPORT Ib

The ligation reaction is used to transform competent *E. coli* DH5-a. The transformed *E. coli* are selected for the presence of plasmid by growing colonies on Lb agar plates with 100 mg/ml ampicilin. Ampicilin resistant colonies are recovered and grown in Lb liquid media with 100 mg/ml ampicilin. Plasmid DNA is purified from the cultures by standard miniprep procedures. The correct construct is verified by the susceptibility for cleavage with Fok I.

9) Cleavage with Fok I

A 5 mg sample DNA is treated with 10 units of Fok I (New England Biolabs) for 60 minutes at 37° C. in a 50 ml reaction consisting of 50 mM potassium acetate, 20 mM Tris-acetate (pH 7.9), 10 mM Mg acetate, 1 mM DTT and 100 mg/ml BSA. The DNA is purified as described above.

10) Klenow Treatment

The Fok I digested DNA is treated with 10 units of DNA polymerase I large (Klenow) fragment (New England Biolabs) for 60 minutes at 37° C. in a 50 ml reaction consisting of 10 mM Tris-acetate (pH 7.5), 5 mM $MgCl_2$, 7.5 mM DTT, 1 mM ATP, 1 mM GTP, 1 mM CTP, 1 mM TTP and 100 mg/ml BSA. The DNA is purified as described above.

11) Cleavage with Hind III

The Klenow-treated DNA is further digested with Hind II and purified as already described.

12) Preparation of pSPORT Ib for Iterative Ligation of Polyester Coding Sequences The plasmid pSPORT Ib is digested with the restriction endonuclease Fok I, which causes the plasmid to become linearized and to have the following termini:

-5'-AGC-ACG-AGG-GGA-AAT-CTG-ATG-3'

-3'-TGCAG-TCG-TGC-TCC-CCT-TTA-GAC-TACATTA-5' and

5'-TAAT-GCATGC-GCG-CATCC-A-3'-

3'-CGTACG-CGC-GTAGG-TTCGA-5'-

Key
Bold=Fok I site

The linearized plasmid is treated with Klenow fragment to fill in the 3' overhangs. The DNA is then cleaved with Hind III. This linearized plasmid is designated pSPORT-La.

4) First Round of Ligation of Polyester Coding Sequence into pSPORT-La

In this step, a set of oligonucleotides is ligated into pSPORT-La between the blunt ended 5' termini and the 3' Hind III termini. The oligonucleotides are synthesized with the following sequence:

5'-AA-TAA-TAA-TAA-TAA-TAA-TAA-TAA-TAA-TAA-TAA-TAA-TAA-TAA-TAA-TAA-TAA-TAA-TAA-GCATGC-GCG-CATCC-A-3'

3'-TT-ATT-ATT-ATT-ATT-ATT-ATT-ATT-ATT-ATT-ATT-ATT-ATT-ATT-ATT-ATT-ATT-ATT-ATT-ATT-ATT-CGTACG-CGC-GTAGG-TTCGA-5'     VI

Key
Bold=Fok I site

The oligonucleotides are combined, heated to 90° C. then allowed to cool slowly to room temperature. During cooling, the oligonucleotides anneal to form a double stranded DNA. The double stranded DNA is ligated into pSPORT-La.

13) Ligation of Oligonucleotide VI into Klenow Treated and Hind III Digested pSPORT-La The Klenow-treated and Hind III digested pSPORT-La DNA is combined with 1 mg of annealed oligonucleotide VI. The DNA solution is treated with 10 units of T4 DNA ligase in a 100 ml reaction consisting of 50 mM Tris-HCl (pH 7.8), 10 mM DTT, 1 mM ATP and 100 mg/ml BSA at 15° C. for 16 hours. The new plasmid, designated pSPORT Ic, has the first segment of the polyester coding region, followed by Fok I and Hind III sites. The sequence is diagramed below (showing only the top strand of the DNA duplex):

-5'-<u>AGC-ACG-AGG-GGA-AAT-CTG</u>-ATG-[TAA]$_{24}$-Fok I-Hind III-3'-     VII

Key
Bold=start codon
Underline=trpA initiator sequence

12) Transformation and Selection of pSPORT Ic

The ligation reaction is used to transform competent *E. coli* DH5-a. The transformed *E. coli* are selected for the presence of plasmid by growing colonies on Lb agar plates with 100 mg/ml ampicilin. Ampicilin resistant colonies are recovered and grown in Lb liquid media with 100 mg/ml ampicilin. Plasmid DNA is purified from the cultures by standard miniprep procedures. The correct construct is verified by the molecular weight.

15) Second Round of Ligation of Polyester-coding Sequence into pSPORT-Ic pSPORT-Ic is prepared for ligation of polyester coding sequence as described above for pSPORT-Ib. The resulting linearized plasmid is designated pSPORT-Lb. A new set of oligonucleotides is synthesized which contains sequences for the next section of the polyester coding sequence:

5'-TAA-TAG-TAA-TAG-TAA-TAG-TAA-TAG-TAA-TAG-TAA-TAG-TAA-TAG-TAA-TAG-TAA-TAG-TAA-TAG-TAG-TAG-TAG-TAG-TAG-TAG-TAG-TAG--GCATGC-GCG-CATCC-A-3'

3'-ATT-ATC-ATT-ATC-ATT-ATC-ATT-ATC-ATT-ATC-ATT-ATC-ATT-ATC-ATT-ATC-ATT-ATC-ATT-ATC-ATC-ATC-ATC-ATC-ATC--CGTACG-CGC-GTAGG-TTCGA-5'     VIII

Key
Bold=Fok I site

The oligonucleotides are combined, heated to 90° C., then allowed to cool slowly to room temperature. During cooling, the oligonucleotides anneal to form a double stranded DNA. The double stranded DNA is ligated into pSPORT-Lb. The resulting new plasmid, designated pSPORT Id, has approximately two thirds of the polyester coding region, followed by Fok I and Hind III sites. The sequence is diagramed below (showing only the top strand of the DNA duplex):

-5-'AGC-ACG-AGG-GGA-AAT-CTG-ATG-[TAA]$_{24}$-[TAA-TAG]$_{10}$-[TAG]$_{10}$-Fok I-Hind III-3'-     IX Key
Bold=start codon
Underline=trpA initiator sequence
16) Third Round of Ligation of Polyester-coding Sequence into pSPORT-Id The plasmid pSPORT-Id is prepared for ligation of the last segment of the polyester coding sequence as described above for pSPORT-Ib. The linearized plasmid is designated pSPORT-Lc. A new set of oligonucleotides is synthesized that contains sequences for the last section of the polyester coding sequence and the STOP codon:

5'-TAG-TAG-TAG-TAG-TAG-TAG-TAG-TAG-TAG-TAG-TAG-TAG-TAG-TAG-TAG-TGA-A-3'

3'-ATC-ATC-ATC-ATC-ATC-ATC-ATC-ATC-ATC-ATC-ATC-ATC-ATC-ATC-ATC-ACT-TTCGA-5'     X

The oligonucleotides are combined, heated to 90° C., then allowed to cool slowly to room temperature. During cooling, the oligonucleotides anneal to form a double stranded DNA. The double stranded DNA is ligated into pSPORT-Lc. The new plasmid, designated pSPORT Ie, contains the entire polyester transcriptional unit. Transformation and selection of the pSPORT Id and pSPORT Ie plasmids are carried out as described above.

C) Synthesis of Polyester-Coding RNA
1) Preparation of the RNA Template

The plasmid pSPORT Ie is linearized with BamH I and subjected to in vitro run off transcription.

2) Cleavage with BamH I

A 5 mg sample DNA is treated with 10 units of BamH I (New England Biolabs) for 60 minutes at 37° C. in a 50 ml reaction consisting of 150 mM NaCl, 50 mM Tris-HCl (pH 7.9), 10 mM $MgCl_2$, 1 mM DTT and 100 mg/ml BSA. The resulting linearized DNA is purified as described above.

3) In vitro Run off Transcription

A 1 mg sample of the linearized BamH I digested DNA is treated with 10 units of SP6 RNA Polymerase (BRL) for 60 minutes at 37° C. in a 50 ml reaction consisting of SP6 promoter-primer, 40 mM Tris-HCl (pH 7.9), 6 mM $MgCl_2$, 2 mM Spermidine-$(HCl)_3$, 1 mM DTT, 0.4 mM rATP, 0.4 mM rGTP, 0.4 mM rCTP, 0.4 mM UTP and 100 mg/m BSA. The reaction is stopped by the addition of sodium dodecyl sulphate (SDS) and the nucleic acids are purified. The DNA is digested with RNase free DNase and the RNA is purified by extraction and precipitation, as described herein for DNA.

III) Synthesis of Sup-tRNAphe-lactate and Sup-tRNAphe-glycolate tRNA molecules for lactate and glycolate are synthesized using the deamination method. In the present example, Sup-tRNA-lactate and Sup-tRNA-glycolate are produced directly in a fermentation process. These tRNA species are then translated in vitro using templates and translation systems as described above.

Genes for yeast $tRNA^{gly}$ and $tRNA^{ala}$ are cloned onto a M13 type phage vector and subjected to site directed mutagenesis. The resulting mutagenized tRNA has new anticodons that recognize stop codons (Sup-$tRNA^{gly}$ and Sup-$tRNA^{ala}$). In this example, the stop codons chosen for $tRNA^{ala}$ and for $tRNA^{gly}$ are UAA and UAG, respectively. The new tRNA genes are cloned onto an appropriate expression vector downstream of an inducible promoter. These plasmids are used to transform yeast. The resulting recombinant yeast strain is used to produce large quantities of Sup-$tRNA^{gly}$-glycine and Sup-$tRNA^{ala}$-alanine.

Cultures of the yeast are grown to near confluence. A protein synthesis inhibitor is added and the inducible tRNA genes are activated. The yeast express the $tRNA^{gly}$ and $tRNA^{ala}$, which are aminoacylated with the appropriate amino acid. The resulting Sup-$tRNA^{gly}$-glycine and Sup-$tRNA^{ala}$-alanine are purified by standard techniques. Purified Sup-$tRNA^{gly}$-glycine and Sup-$tRNA^{ala}$-alanine are incubated in 0.25 M sodium acetate, 0.01 M magnesium acetate, 1M $NaNO_2$ at 24° C. The pH is maintained at pH 4.3 with acetic acid. These reaction conditions result in the deamination of the amino acids on the tRNA to the a-hydroxyael analogs as shown in FIG. 5. The resulting Sup-tRNAgly-glycolate and Sup-$tRNA^{ala}$-lactate are purified by column chromatography.

IV) INITIATOR tRNAf

Protein synthesis is specifically initiated at the first AUG codon. The process of initiation involves a unique tRNA called tRNAf. This tRNAf is normally aminoacylated with methionine to generate Met-tRNAf. The charged tRNAf is then converted to Formylmethionyl-tRNAf, or fMET-tRNAf. The initiation factors for protein synthesis specifically recognize fMET-tRNAf, and initiate translation using this tRNA at the first AUG codon.

To provide the initiator tRNA for polyester synthesis, a synthetic initiator tRNA is synthesized such that it recognizes the AUG codon, but carries a lactate instead of methionine. A truncated version of the E. coli tRNAf is generated that does not have the CpA dinucleotide at the 3' termini. A synthetic CpA dinucleotide is synthesized and coupled with lactate to form CpA-lactate. The CpA-lactate is ligated onto the 3' termini of the truncated tRNAf. The resulting Lactate-tRNAf initiates translation by recognizing the AUG codon; however, translation is initiated with lactate rather than methionine. In the present example, the starting tRNAf must be E. coli so that it will be recognized by the initiation factors in the E. coli in vitro translation system.

V) In vitro Translation of Polyester Template

In the present example, an E. coli in vitro translation system is employed. E. coli amino-acyl tRNA transferase cannot amino-acylate yeast tRNA, which in this example is the origin of the Sup-$tRNA^{phe}$-glycolate. Thus, it will be appreciated that once the Sup-tRNAphe-lactate and Sup-tRNAphe-glycolate participate in a translation cycle, the free Sup-$tRNA^{phe}$ will not be amino-acylated with phenylalanine and thus interfere with polyester synthesis. In addition, the E. coli strain used to generate the in vitro translation extract is a recombinant strain that does not express tRNA for the two stop codons used to encode glycolate and lactate. Therefore, native tRNA will not compete with Sup-$tRNA^{phe}$-glycolate for recognition of stop codons.

The translation extract is used to synthesize polymers in conjunction with the artificial template. Free amino acids, ATP, GTP, Sup-$tRNA^{phe}$-lactate and Sup-$tRNA^{phe}$-glycolate, and template are added to the E. coli extract. Translation is terminated by the addition of a detergent, and amide-polyester polymers are purified by column chromatography. The purified polymer is processed by the cleavage steps described earlier to separate the amide from the polyester segment. If desired, the polyester segment is further purified by extraction methods or additional column chromatography.

The RNA template for the polyester is combined with a cell free E. coli translation system. A pool of the Sup-$tRNA^{phe}$-lactate and Sup-$tRNA^{phe}$-glycolate is added, along with ATP and GTP. In addition, Lactate-tRNAf or MET-tRNAf is added.

VI) Purification and Processing of the Polyester

The polyester is purified from the in vitro translation reaction by extraction in methylene chloride followed by further purification by gel permeation chromatography.

Since the polyester of the present example is synthesized with Lactate-tRNAf, no further processing is required.

EXAMPLE II

Template Directed Synthesis of a Polyester with a Polypeptide Leader Sequence

I) Designation of Polyester Sequence

In the present example, a polyester having the sequence I (as in Example I) is produced. It differs from the polyester of Example I in that it includes a polypeptide leader sequence, as described below.

II) Design and Synthesis of the Synthetic Gene

A) The Polyester Coding Region

This section of the template is identical to that described in Example I.

B) Stepwise Construction of the Transcriptional Unit

1) E. coli Fusion Protein Expression Vector

Since in vitro translation of the synthetic mRNA is carried out in an E. coli cell free system, the initiator region must be recognized by E. coli ribosomes. In this example, the fusion protein expression vector pMAL-p2 (New England Biolabs) is used. This commercially available vector is used to express fusion protein in E. coli. Therefore, all of the necessary initiator sequences are already present, along with the template for the polypeptide leader sequence.

2) First Round of Ligation of Polyester Coding Sequence into pMAL-p2

The following Oligonucleotides are synthesized:

5'-TAA-TAA-TAA-TAA-TAA-TAA-TAA-TAA-TAA-TAA-TAA-
TAA-TAA-TAA-TAA-TAA-TAA-TAA-TAA-TAA-TAA-TAA-
GCATGC-GCG-CATCC-A-3'

3'-ATT-ATT-ATT-ATT-ATT-ATT-ATT-ATT-ATT-ATT-ATT-ATT-
ATT-ATT-ATT-ATT-ATT-ATT-ATT-ATT-ATT-ATT-CGTACG-
CGC-GTAGG-TTCGA-5'                                    XI

Key
Bold=Fok I site
Underline=Hind III adaptors

The oligonucleotides are combined, heated to 90° C., then allowed to cool slowly to room temperature. During cooling, the oligonucleotides anneal to form a double stranded DNA. The double stranded DNA is ligated into pMAL-p2 that has been digested with XmnI and Hind III. The new plasmid, pMAL-p2a, has the first section of the polyester coding sequence ligated in frame with the polypeptide leader sequence.

3) Second Round of Ligation of Polyester Coding Sequence into pMAL-p2a

To initiate the second round of template construction, pMAL-p2a is digested with Fok I, treated with Klenow fragment, then digested with Hind III. The linearized version of pMAL-p2a is designated pMAL-p2aL. The following oligonucleotides are synthesized:

5'-TAA-TAA-TAA-TAA-TAG-TAA-TAG-TAA-TAG-TAA-TAG-
TAA-TAG-TAA-TAG-TAA-TAG-TAA-TAG-TAA-TAG-TAA-
TAG-GCATGC-GCG-CATCC-A-3'

3'-ATT-ATT-ATT-ATT-ATC-ATT-ATC-ATT-ATC-ATT-ATC-ATT-
ATC-ATT-ATC-ATT-ATC-ATT-ATC-ATT-ATC-ATT-ATC-CG-
TACG-CGC-GTAGG-TTCGA-5'                               XII

The oligonucleotides are combined, heated to 90° C., then allowed to cool slowly to room temperature. During this time the oligonucleotides anneal to form a double stranded DNA. The double stranded DNA is ligated into pMAL-p2aL. The new plasmid, designated pMAL-p2b, has two-thirds of the polyester coding sequence ligated in frame with the polypeptide leader sequence.

4) Third Round of Ligation of Polyester Coding Sequence into pMAL-p2a

To initiate the third round of template construction, pMAL-p2b is digested with Fok I, treated with Klenow fragment, then digested with Hind III. The linearized version of pMAL-p2b is designated pMAL-p2bL. The following oligonucleotides are synthesized:

5'-TAG-TAG-TAG-TAG-TAG-TAG-TAG-TAG-TAG-TAG-TAG-
TAG-TAG-TAG-TAG-TAG-TAG-TAG-TAG-TAG-TAG-TAG-
TAG-TAG-TAG-TGA-GCATGC-GCG-CATCC-A-3'

3'-ATC-ATC-ATC-ATC-ATC-ATC-ATC-ATC-ATC-ATC-ATC-
ATC-ATC-ATC-ATC-ATC-ATC-ATC-ATC-ATC-ATC-ATC-
ATC-ATC-ATC-ACT-CGTACG-CGC-GTAGG-TTCGA-5'   XIII

The oligonucleotides are combined, heated to 90° C., then allowed to cool slowly to room temperature. During this time the oligonucleotides anneal to form a double stranded DNA. The double stranded DNA is ligated into pMAL-p2aL. The new plasmid, designated pMAL-p2C, has the complete polyester coding sequence ligated in frame with the polypeptide leader sequence.

C) Synthesis of Polyester-Coding RNA

1) Preparation of the RNA Template pMAL-p2c is used to transform E. coli strain DH5a. The E. coli is grown to stationary phase and IPTG is added to initiate transcription of the RNA for the polypeptide-polyester fusion protein. After 1–2 hours the E. coli are collected and total RNA is purified by standard methods. The RNA template is purified from the total RNA by affinity chromatography using a column that has covalently attached oligonucleotides that anneal to the template sequence.

III) Synthesis of Sup-tRNAphe-Lactate and Sup-tRNAphe-Glycolate

The tRNA molecules for lactate and glycolate are synthesized as described in Example I.

IV) In vitro Translation of Polyester Template

The RNA template is prepared as described in Example I. The RNA template for the polyester is combined with a cell free E. coli translation system. A pool E. coli tRNA, Sup-tRNA$^{phe}$-lactate and Sup-tRNA$^{phe}$-glycolate and ATP and GTP are added. The translation reaction is terminated with the addition of SDS.

V) Purification and Processing of the Polyester

The polypeptide-polyester fusion polymer is purified from the in vitro translation reaction by affinity chromatography. The polypeptide region of the fusion polymer encoded by the pMAL-p2 vector is the maltose binding protein. The fusion polymer is separated from the in vitro reaction mixture by passing the sample through an amylose column. The polymer binds to the amylose by virtue of the maltose binding protein segment. The fusion polymer is eluted from the column with free maltose.

The polypeptide portion of the fusion polymer is cleaved from the polyester segment by treatment with cyanogen bromide.

What is claimed is:

1. A medical device or article comprising a synthetic polymer which is biocompatible, wherein the synthetic polymer comprises a lactic acid and glycolic acid ester copolymer having the following formula:

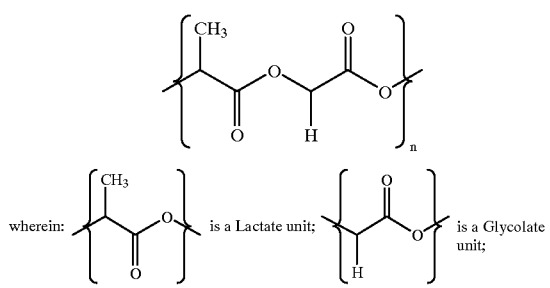

wherein: 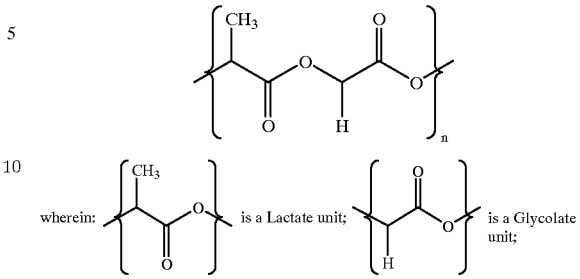

n is the total number of Lactate units plus the total number of Glycolate units divided by 2; the positions of Lactate and Glycolate within each unit of the formula are independently interchangeable; and the value of n and the position of Lactate and Glycolate within each unit of the formula is predetermined.

2. The medical device or article of claim 1, wherein said medical device or article is selected from the group consisting of sutures, staples, clips, drug delivery devices, pins and screws.

3. The medical device or article of claim 1 which is absorbable.

4. The medical device or article of claim 2, additionally comprising one or more medicinal agents.

5. The medicinal device or article of claim 4, wherein said medicinal agents are selected from the group consisting of antimicrobials, analgesics, antipyretics, anesthetics, antiepileptics, antihistamines, anti-inflammatories, cardiovascular drugs, diagnostic agents, sympathomimetics, cholinomimetics, anti-muscarinics, antispasmodics, hormones, growth factors, muscle relaxants, adrenergic neuron blockers, anti-neoplastics, immunosuppressants, gastrointestinal drugs, diuretics, steroids and enzymes.

6. The medical device or article of claim 1, wherein said lactic acid and glycolic acid polyester copolymer is synthesized by a process comprising:
 a. altering Supp.tRNA so as to accept lactic acid and glycolic acid, to produce Supp.tRNA$^{lac}$ and Supp.tRNA$^{gly}$ respectively;
 b. preparing an mRNA sequence including triplet codons recognized by the Supp.tRNA$^{lac}$ and Supp.tRNA$^{gly}$ of step (a);
 c. providing an expression translation system;
 d. introducing into the system of step (c) the products of steps (a) and (b) under conditions which allow the production of lactic acid glycolic acid polyester copolymer; and
 e. collecting the copolymer produced in step (d).

7. A suture substantially as shown in FIG. 2, comprising a synthetic polymer which is biocompatible, wherein the synthetic polymer comprises a lactic acid and glycolic acid ester copolymer having the following formula:

n is the total number of Lactate units plus the total number of Glycolate units divided by 2; the positions of Lactate and Glycolate within each unit of the formula are independently interchangeable; and the value of n and the position of Lactate and Glycolate within each unit of the formula is predetermined.

8. The suture of claim 6 which is absorbable.

9. The suture of claim 6, additionally comprising one or more medicinal agents.

10. The suture of claim 9, wherein said medicinal agents are selected from the group consisting of antimicrobials, analgesics, antipyretics, anesthetics, antiepileptics, antihistamines, anti-inflammatories, cardiovascular drugs, diagnostic agents, sympathomimetics, cholinomimetics, anti-muscarinics, antispasmodics, hormones, growth factors, muscle relaxants, adrenergic neuron blockers, anti-neoplastics, immunosuppressants, gastrointestinal drugs, diuretics, steroids and enzymes.

11. A method of closing a wound in living tissue comprising approximating tissue and passing a needled suture as in any of claims 7, 8, 9 or 10 through tissue to create wound closure; tying the suture in a knot; and removing the needle from the suture; thereby closing the wound.

12. A process for the manufacture of monofilament sutures comprising: melt extruding polyester resin to provide a monofilament; stretching the solidified monofilament at a temperature above ambient in water or other suitable liquid or gaseous medium; to provide a stretched monofilament; wherein the polyester resin is comprised of a synthetic polymer which is bioresorbable, wherein the synthetic polymer comprises a lactic acid and glycolic acid polyester copolymer in which each successive lactic acid and glycolic acid monomeric unit in the polyester copolymer has been individually and specifically determined.

* * * * *